(12) United States Patent
Shaik et al.

(10) Patent No.: US 9,447,346 B2
(45) Date of Patent: Sep. 20, 2016

(54) TWO-STEP PROCESS FOR PRODUCTION OF RON-ENHANCED MIXED BUTANOLS AND DIISOBUTENES

(71) Applicant: Saudi Arabian Oil Company, Dhahran (SA)

(72) Inventors: Kareemuddin M. Shaik, Dhahran (SA); Wei Xu, Dhahran (SA); Thamer Mohammed, Dhahran (SA); Hassan Babiker, Dhahran (SA); Gautam Tavanappa Kalghatgi, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 14 days.

(21) Appl. No.: 14/103,439

(22) Filed: Dec. 11, 2013

(65) Prior Publication Data
US 2015/0159102 A1    Jun. 11, 2015

(51) Int. Cl.
*C10L 1/182* (2006.01)
*C10L 10/10* (2006.01)
(Continued)

(52) U.S. Cl.
CPC .................. *C10L 1/182* (2013.01); *C07C 2/18* (2013.01); *C07C 2/28* (2013.01); *C07C 29/04* (2013.01); *C07C 29/82* (2013.01); *C10G 50/00* (2013.01); *C10L 1/1608* (2013.01); *C10L 10/10* (2013.01); *C07C 2527/19* (2013.01); *C07C 2527/199* (2013.01); *C07C 2531/10* (2013.01); *C10G 2300/305* (2013.01); *C10G 2400/02* (2013.01);
(Continued)

(58) Field of Classification Search
CPC .......... C10L 10/10; C10L 1/16; C10L 1/182; C10L 2200/04; C10L 2270/023; C10L 2290/06; C10L 2290/46; C10L 2290/54; C10L 2300/20; C07C 2/18; C07C 29/04; C07C 29/82; C07C 2/28; C07C 2527/19; C07C 2527/199; C07C 2531/10; C10G 50/00; C10G 2300/305; C10G 2400/02
USPC .................................................. 44/451, 453
See application file for complete search history.

(56) References Cited

U.S. PATENT DOCUMENTS

| 4,087,471 A | 5/1978 | Bowman et al. |
| 4,100,220 A | 7/1978 | Bowman et al. |

(Continued)

FOREIGN PATENT DOCUMENTS

| EP | 0 994 088 | 4/2000 |
| EP | 994088 A1 * | 4/2000 |

(Continued)

OTHER PUBLICATIONS

Mahajani, S. M. et al., "Extractive hydration of n-butene with solid acid catalysts in the liquid phase and under supercritical conditions" Chemical Engineering Science 56 (2001) 5625-5633.

(Continued)

*Primary Examiner* — James Goloboy
*Assistant Examiner* — Latosha Hines
(74) *Attorney, Agent, or Firm* — Leason Ellis LLP (57) ABSTRACT

A two-step process for the oligomerization and hydration of a mixed butenes feed is provided and is implemented in a two-stage system. The two-step process yields a product consisting of diisobutenes (DIBs) and mixed butanols. The DIBs are produced via the selective oligomerization of isobutene in a first stage and the mixed butanols are produced via the hydration, in a second stage, of mixed butenes that remain unreacted in the first stage.

23 Claims, 2 Drawing Sheets

(51) Int. Cl.
  *C10L 1/16* (2006.01)
  *C07C 2/18* (2006.01)
  *C07C 29/04* (2006.01)
  *C07C 29/82* (2006.01)
  *C07C 2/28* (2006.01)
  *C10G 50/00* (2006.01)

(52) U.S. Cl.
  CPC ...... *C10L 2200/04* (2013.01); *C10L 2270/023* (2013.01); *C10L 2290/06* (2013.01); *C10L 2290/46* (2013.01); *C10L 2290/54* (2013.01); *C10L 2300/20* (2013.01)

(56) References Cited

U.S. PATENT DOCUMENTS

| | | |
|---|---|---|
| 4,351,970 A | 9/1982 | Sommer et al. |
| 6,500,999 B2 | 12/2002 | Di Girolamo et al. |
| 6,660,898 B1 | 12/2003 | Pyhälahti et al. |
| 7,002,053 B2 | 2/2006 | Nierlich et al. |
| 8,558,036 B2 | 10/2013 | Xu |
| 2005/0283038 A1* | 12/2005 | Kuechler et al. ............. 585/639 |
| 2012/0117862 A1 | 5/2012 | Xu |
| 2013/0104449 A1* | 5/2013 | Xu et al. .................. 44/452 |

FOREIGN PATENT DOCUMENTS

| | | |
|---|---|---|
| EP | 2374780 | 10/2011 |
| WO | WO 02/36528 | 5/2002 |
| WO | WO 2010056257 | 5/2010 |
| WO | WO 2012/095744 | 7/2012 |

OTHER PUBLICATIONS

Miao Sun, et al., "Significant Effect on Acidity on Catalytic Behaviors of Cs-Substituted Polyoxometalates for Oxidative Dehydrogenation of Propone," Applied Catalysis A: General (2008); pp. 212-221.

* cited by examiner

Fig. 1

Fig. 2: Effect of Blend Components on RON

TWO-STEP PROCESS FOR PRODUCTION OF RON-ENHANCED MIXED BUTANOLS AND DIISOBUTENES

TECHNICAL FIELD

The present invention relates to a process for the production of mixed alcohols along with butene oligomers. More specifically, the present invention relates to a two-step process for oligomerizing and hydrating a feed stream that includes butene isomers to produce butene oligomers and mixed butanols, which can be used as blending components with reduced RVP and increased RON and octane sensitivity.

BACKGROUND

While hydrocarbon fuels remain as the dominant energy resource for internal combustion engines, alcohols, especially methanol and ethanol, have also been used as fuels. Currently, the primary alcohol fuel is ethanol, which is commonly blended into gasoline in quantities of 5 to 10%. In fact, various fuels being produced today consist primarily of alcohols. For example, E-85 fuel contains 85% ethanol and 15% gasoline, and M-85 fuel has 85% methanol and 15% gasoline. While ethanol possesses excellent octane enhancement properties, there are several drawbacks to its use as a gasoline component, including: energy deficiencies (ethanol provides approximately 39% less energy than gasoline), high blending Reid Vapor Pressure (RVP) (at 10% of blending, the RVP=11 psi), and incompatibility with existing transportation facilities.

Historically, lead (Pb) was added to gasoline to increase its octane rating and thereby improve its antiknock properties. However, the use of lead in gasoline has now been eliminated in most countries for health and environmental reasons. In response to the need to increase octane ratings in the absence of lead, methyl-tertiary-butyl-ether (MTBE) was commercially introduced as an octane enhancing component of gasoline in the United States and other countries in the late 1970s. Legal restrictions on the minimum oxygen content of some gasolines—introduced in the 1990s as a means of reducing environmentally harmful exhaust emissions—encouraged a further increase in the concentration of MTBE in gasoline, which, by then, was being blended at up to 15% by volume. While MTBE is still widely used in the United Kingdom, its use has been in gradual decline in other regions of the world due to concerns about the harmful effects of MTBE itself. Specifically, its existence in groundwater has led to a decline in its use in countries such as the United States, where some states have actively legislated against its use. Today, in order to meet performance and legal requirements, the fuel industry in the United States is now replacing MTBE with fermented grain ethanol. However, producing the necessary quantities of grain ethanol to replace MTBE is problematic in specific regions, and the use of ethanol as a gasoline component has other drawbacks as discussed above.

Certain other alcohols (i.e., butanols), as well as butene oligomers (e.g., diisobutenes (DIBs)) can be used as combustible neat fuels, oxygenate fuel additives, or constituents in various types of fuels. The BTU content of butanols and diisobutenes is closer to the energy content of gasoline than either methanol or ethanol. Butanols have been thought of as second generation fuel components after ethanols. Specifically, 2-butanol and tert-butanol can be particularly advantageous fuel components, as they have blending octane sensitivities and energy densities comparable to those of MTBE and have been shown to have lower RVP at 15% concentrations relative to comparable ethanol blends. Similarly, DIB is a non-oxygenated fuel component with many advantages over other fuel additives. For instance, DIBs have higher RON, better anti-knock quality, and higher energy content compared with MTBE, as well as a lower RVP than MTBE, butanols and ethanol.

Butanols can be produced via the hydration of butenes, a process that typically utilizes an acid catalyst. While the production of butanols via hydration of butenes is a commercially important process, it is typically very costly. DIBs are produced via the oligomerization/dimerization of butenes, in particular isobutene. The dimerization of isobutene is also generally performed using acid catalysts, such as sulfuric acid and hydrogen fluoride; however, these catalysts tend to be highly corrosive in nature.

Both butanols and DIBs provide certain advantages over other existing fuel components. However, until now, there have not been any processes in place that are particularly effective for converting mixed olefins into alcohols—especially butenes into butanols—while also dimerizing part of the mixed olefins feed into oligomers such as DIBs without requiring the costly separation of either mixed butenes isomers in the feed or the mixed butanol isomers in the product. The combination of butanols and DIBs as a fuel additive would lead to enhanced RON, octane sensitivity, and energy density, as well as decreased RVP in gasoline.

Thus, there is a need for alternative gasoline oxygenates that possess comparable RON enhancement properties and a higher energy content than MTBE and ethanol, but that also eliminates the environmental and compatibility concerns of MTBE and ethanol. Additionally, there is a need for alternative fuel additives that lower the RVP of fuel in the absence of MTBE. Finally, there is a need for an alternative process that allows for both the hydration and oligomerization of mixed butenes to alcohols and oligomers, namely butanols and DIB, which can be used as octane enhancing components.

SUMMARY

The present invention is directed to a process for producing RON-enhanced mixed butanols, potential replacement oxygenates for MTBE and ethanol as fuel additives. More specifically, this invention relates to a two-step process (two-stage system) for producing DIBs and mixed butanols from the oligomerization and hydration of a mixed butene feed containing a mixture of the four butene isomers: 1-butene, 2-cis-butene, 2-trans-butene and isobutene. The DIBs are produced via the selective oligomerization of isobutene (in the absence of water) in a first reactor containing an oligomerization catalyst, while the other butene isomers remain primarily unreacted. In one embodiment, at least a majority of and preferably, at least a substantial portion of the isobutene is oligomerized (dimerized) to form DIBs. The mixed butanols are produced via the hydration of the butene feed in a subsequent second reactor containing a hydration catalyst. In a preferred embodiment, the n-butenes (1 and 2-butenes) hydrate to form 2-butanol and any remaining isobutene hydrates to form tert-butanol.

In one embodiment, the temperature maintained in the both reactors is 80-250° C. and the pressure maintained in the reactors is approximately 10-80 bar.

In another embodiment, the temperature maintained in the olimerization reactor is 30-100° C. and the pressure maintained in the reactors is approximately 5-80 bar while the temperature maintained in the hydration reactor is 100-250° C. and the pressure maintained in the reactors is approximately 10-80 bar.

This invention provides a distinct advantage over other oligomerization and hydration processes, as it allows for enhanced control over the quantities of DIB and tert-butanol produced. Because DIB has a lower RPV, higher RON, octane sensitivity, and energy content compared with tert-butanol, a product with greater DIB content relative to tert-butanol is preferred for gasoline blending purposes. Thus, the ability to increase the production of DIB via oligomerization while decreasing the yield of tert-butanol via hydration results in a RON-enhanced mixed butanol final product that possesses superior gasoline blending properties.

BRIEF DESCRIPTION OF THE DRAWING FIGURES

A more complete understanding of the invention and its many features and advantages will be attained by reference to the following detailed description and the accompanying drawing. It is important to note that the drawing illustrates only one embodiment of the present invention and therefore should not be considered to limit its scope.

DETAILED DESCRIPTION OF CERTAIN EMBODIMENTS

As mentioned hereinbefore, the prior art contains a number of processes for the oligomerization of mixed butenes and processes for the hydration of olefins into alcohols; however, until now, there have not been any processes in place that are particularly effective for converting a mixed butene feed into butanols, while also oligomerizing part of the mixed butene feed into oligomers such as DIBs.

The present invention overcomes the deficiencies and limitations of the prior art and is directed to a two-step process for the oligomerization and hydration of mixed butenes to produce a mixed butanols and DIB product, which can being used as superior gasoline blending components. As described herein, the two-step process of the present invention allows for improved control over the composition (amount percentage) of the DIBs in the final product, thereby allowing the composition of the final product stream to be tailored.

Mixed Olefins (Butenes)

Mixed butenes have four structural isomers: 1-butene, 2-cis-butene, 2-trans-butene, and isobutene. Optionally, other low olefins, such as propylene and ethylene, can also be present in the feed as described below.

Diisobutenes (DIBs) or Isooctenes

Diisobutenes include two isomers of 2,4,4-tri-methyl-1-pentene and 2,4,4-trimethyl-2-pentene.

Mixed Butanols

Mixed butanols include at least two of the following compounds: 1-butanol, 2-butanol, tert-butanol, and isobutanol. Preferred embodiments of the present invention include only 2-butanol and tert-butanol as described below.

Oligomerization (Dimerization)

Oligomerizations of mixed butenes as described herein include oligomerizations of all butene isomers, preferably oligomerizations of isobutene and more preferably, the dimerization of isobutene. The oligomerization fraction can be extremely rich in dimers (isooctenes or DIBs), and can be added as such to the gasoline cuts to give a very high quality gasoline.

Major compounds that can be derived from the oligomerization of mixed butenes include but are not limited to: diisobutenes (DIBs), tri-isobutenes, dimer of isobutene and n-butenes, and trimer of isobutene and, n-butenes can all be derived from the oligomerization of mixed butenes. It will be appreciated by one of skill in the art that other products can be formed. As is known, DIB is a non-oxygenative fuel component with many advantages as a blending agent, such as higher RON, higher octane sensitivity or better anti-knock quality, higher energy content compared to MTBE and alkylates, and/or lower RVP than MTBE and ethanol.

Dimerization of Isobutene

Hydration of Mixed Butenes

Hydration of butenes to butanols are commercially important reactions as the products find several important industrial applications. Generally, the hydration of mixed butenes is selected to only produce 2-butanol and tert-butanol; however, the formation of other compounds is possible. Mixed butanols, primarily 2-butanol and tert-butanol, can be used as oxygenative-type premium gasoline additives.

Other possible products that can be derived from the hydration of mixed butenes include but are not limited to etherification products of butanols and butenes or butanols itself. Butanols generally have good gasoline octane blending characteristics and can be used in combination as petroleum additives with other oxygenates, such as ethanol and MTBE.

The Present Oligomerization/Hydration Process

As described herein, processes for production of mixed butanols and butene oligomers from a mixed butene feed are provided as embodiments of the present invention. Additionally, processes for producing fuel compositions that include oligomers and alcohols prepared from butene are also provided as embodiments of the present invention.

In one embodiment of the present invention, a method (process) for producing alcohols and oligomers from olefins is provided. More specifically, the process is a two-step process in which mixed olefins are oligomerized in the absence of water in the first step and hydration of the remaining mixed olefins takes place in the second step with adequate unit operations to separate the products as needed and described herein. A product stream that includes oligomers and alcohols is formed. In certain embodiments, the mixed olefins are in the form of a feedstock that is a mixed butene feedstock and the product stream includes DIBs and mixed butanols. In one embodiment, the product stream that includes DIBs and mixed butanols can be combined with a fuel component to produce a fuel composition. The fuel component of the fuel composition can be selected from gasoline, diesel, jet fuel, aviation gasoline, heating oil, bunker oil, or combinations thereof. In certain embodiments, the resultant fuel composition will have increased RON and reduced RVP, without the presence of other chemicals that can have deleterious effects on the environment.

The source of the mixed olefin (butene) stream can vary and can encompass any number of different sources of feedstocks (streams) that are suitable for use in the present invention. In some embodiments of the present invention, the mixed olefin stream can be discharge stream from an FCC unit or thermal cracking unit, raffinates from an MTBE process, a raffinates stream from TBA process, a liquefied petroleum gas (LPG) stream, or combination thereof. In one embodiment, the mixed olefin (butene) feed comes from a refinery gas stream.

Various types of olefins can be included in the mixed olefin stream. As mentioned herein, in certain embodiments, mixed olefin stream can include a mixed butene stream. In another embodiment, the mixed olefin stream can include propylene, n-butene, 2-butene, isobutylene, pentenes, hexenes, olefins having more than 6 carbons with at least two butenes, or combinations thereof. Other olefins that can be used in accordance with other embodiments include ethylene, propene, butenes, pentenes, or other higher olefins. It will be understood that other suitable sources for the mixed olefin stream and types of olefins can used so long as they are suitable for the intended application described herein and achieve a product stream having the desired characteristics that are set forth herein. In yet another embodiment, the mixed butene feed used in the present invention typically contains the four butene isomers in varying quantities as set forth below.

Most commercialized butene hydration processes are designed either with pure feeds, like 1-butene and isobutene, or mixed feeds for the selective isobutene hydration. The process conditions are typically selected to maximize the yield of either 2-butanol or the yield of t-butanol. Because both 2-butanol and t-butanol are valuable oxygenates and octane enhancers for fuels, certain embodiments of the present invention use a two-stage (two-step) based system and process that is effective for the production of highly desired butanols, such as 2-butanol and t-butanol, and butene oligomers for gasoline components from cheap mixed butenes.

With respect to the oligomerization of olefins, different butene isomers have different activities toward dimerization or oligomerization. For example, it is typically difficult for 2-butenes to form the correspondent dimers or oligomers. In contrast, isobutene is predisposed to being dimerized or oligomerized.

In accordance with one embodiment of the present invention, the present two-stage process is such that isobutene is selectively oligomerized (dimerized) to DIB during the oligomerization reaction and the other butenes remain primarily unreactive due to the catalyst selection and/or operating (reaction) conditions. During the hydration phase of the process, all four isomers of butene can be effectively hydrated to form mixed butanols. The resultant product stream thus includes DIBs and mixed butanols.

As described herein, the catalyst systems of the present invention are configured to perform the intended functions in the two different stages, namely, the oligomerization stage and the hydration stage, of the present system/process. Accordingly, the present invention entails the use of an oligomerization catalyst and a hydration catalyst. It will be appreciated that the amount of each catalyst can vary depending upon the mixed olefin stream being sent to the process. It will be appreciated that any number of suitable catalysts can be used for the oligomerization catalyst and the hydration catalyst so long as the respective catalyst operates in the manner described herein and achieves the intended objectives. In one embodiment, the oligomerization catalyst and/or the hydration catalyst comprise an acidic catalyst, such as ionic exchange resins (catalysts). Alternatively, the oligomerization catalyst and/or the hydration catalyst comprise substituted/non-substituted heteropoly acids. For example, a heteropoly acid (cesium substituted) can be prepared according to a process described in Miao Sun, et al., "Significant Effect on Acidity on Catalytic Behaviors of Cs-Substituted Polyoxometalates for Oxidative Dehydrogenation of Propone," *Applied Catalysis A: General* (2008); pp. 212-221, which is hereby incorporated by reference in its entirety. Commonly owned U.S. patent application Ser. No. 14/091,137, which is hereby incorporated by reference in its entirety, sets forth catalysts that can be used as catalysts for use in the present invention.

The oligomerization catalyst and hydration catalyst can be the same or they can be different catalysts.

Figure 1:
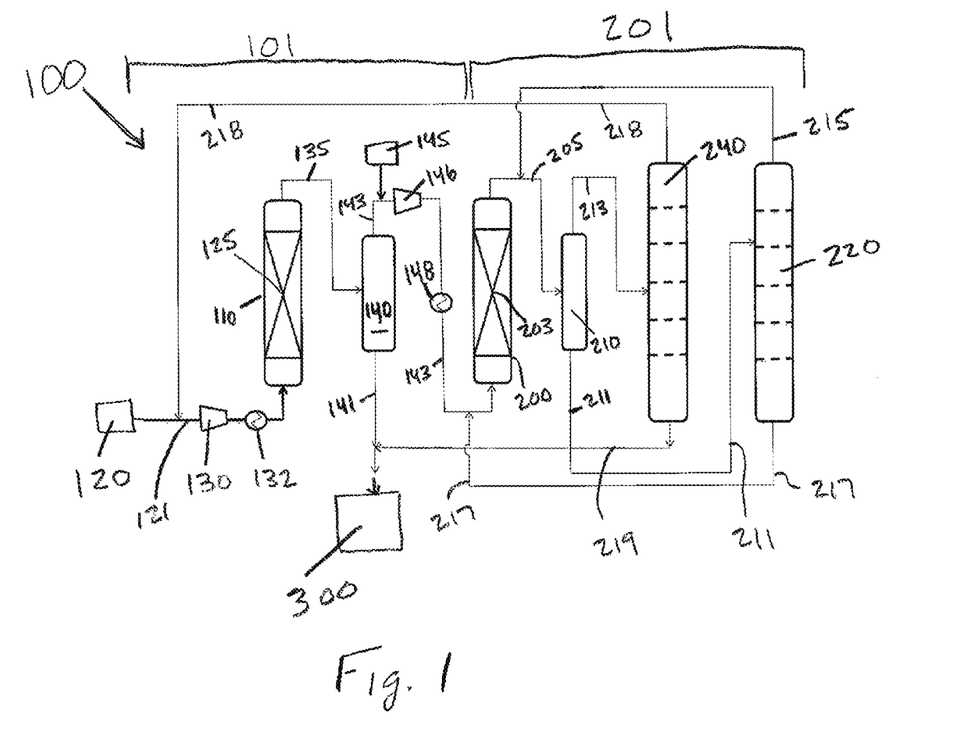
FIG. 1 shows a diagram of a two-step process in accordance with an embodiment of the invention.

FIG. 1 illustrates one exemplary system 100 for performing the oligomerization and hydration of mixed olefins (butenes) in a two-stage process in accordance with the present invention. FIG. 1 likewise shows an exemplary flow scheme. The system 100 can thus be thought of as including two different stages, namely, a first stage, identified at 101, in which the oligomerization of the olefins (butenes) occurs and a second stage, identified at 201, in which the hydration of the olefins (butenes) occurs. As described herein, each stage has associated equipment and an associated catalyst to produce the intended products.

The first stage 101 includes a first reactor 110 in the form of an oligomerization reactor and the second stage 201 includes a hydration reactor 200.

The reactants are delivered to the oligomerization reactor 110 and the hydration reactor 200 in the following manner. A source of feedstock (e.g., a mixed olefin feed and more particularly, a mixed butenes feed) is identified at 120 and is fluidly connected (e.g., by means of a fluid conduit 121 (such as a pipe)) to the oligomerization reactor 110. Before entering an inlet of the oligomerization reactor 110, the feedstock passes through a first compressor 130 and a first heat exchanger 132 that are disposed along the conduit 121 between the source of feedstock 120 and the oligomerization reactor 110. The heat exchanger 132 is located downstream of the compressor 130.

The compressor 130 and the heat exchanger 132 are configured to adjust the pressure and temperature, respectively, of the feedstock prior to it entering the oligomerization reactor 110 and thus also control the oligomerization reactor pressure and temperature. In one exemplary embodiment, the oligomerization reactor conditions are: a pressure between about 10 bar and about 70 bar and a temperature between about 30° C. and about 160° C. In other words, the first compressor 130 serves to compress the mixed butene feed stream to between about 10 bar and about 70 bar and the first heat exchanger 132 serves to adjust the temperature of this mixture to between about 100° C. and about 160° C.

The oligomerization reactor 110 is configured to perform oligomerization of the feedstock introduced therein and under oligomerization conditions. The oligomerization reactor 110 can be in the form of a single stage reactor having an inlet connected to the conduit 121 to receive the feedstock 120. Within the reactor 110, an oligomerization catalyst 125 is contained. For example, the oligomerization catalyst 125 can be located in one or more zones or regions of the reactor 110.

As described below in greater detail, the oligomerization catalyst 125 is of a type which oligomerizes a mixed olefin feedstock under oligomerization conditions. More specifically, the oligomerization catalyst 125 is of a type and is selected so as to cause the oligomerization of isobutene (in the olefin feedstock) to DIBs, while the remaining mixed butenes remain inert (i.e., unreacted). In other words, the oligomerization catalyst 125 is selected so as to selectively oligomerize the isobutene in the feedstock but does not oligomerize the other isomers of butene, thereby leaving these other isomers unreacted (i.e., the unreacted n-butenes and any unreacted isobutene). As a result, the first stage can maximize DIBs production and thus, the final product stream can include optimal DIBs content.

The remaining unreacted mixed butenes and DIB form a first product stream that exits the oligomerization reactor 110 via a conduit 135 and is introduced to a low pressure separator 140. In the low pressure separator 140, the DIB component of the first product stream is removed via conduit 141 for collection, while the unreacted butene stream exits via a different conduit 143. In other words, the low pressure separator 140 is configured and is operated under conditions to separate DIB from the other constituents of the first product stream (i.e., separation of an oligomerized component from an unreacted component).

Upon exiting the low pressure separator 140 via conduit 143, the unreacted mixed butene stream is then contacted with a fresh water stream 145 at a location along the conduit 143. The fresh water stream 145 mixes with the unreacted mixed butene stream to produce a mixture that flows within the conduit 143 to a second compressor 146 and second heat exchanger 148 that are disposed along the conduit 143, with the second heat exchanger 148 being disposed downstream of the second compressor 146. After flowing through both the second compressor 146 and the second heat exchanger 148, the mixture flows to the hydration reactor 200. The second compressor 146 and the second heat exchanger 148 are again configured to adjust the pressure and temperature, respectively, of the feedstock prior to it entering the hydration reactor 200 and thus also control the hydration reactor pressure and temperature. In one exemplary embodiment, the hydration reactor 200 conditions are: a pressure between about 10 bar and about 70 bar and a temperature between about 100° C. and about 160° C. In other words, the second compressor 146 serves to compress the liquid mixture to between about 10 bar and about 70 bar and the second heat exchanger 148 serves to adjust the temperature of this mixture to between about 100° C. and about 160° C.

The hydration reactor 200 is loaded with a hydration catalyst 203 (such that the catalyst is located in one or more zones). As described below in greater detail, the hydration catalyst 203 is of a type which hydrates the mixture of fresh water and unreacted mixed butene stream under hydration conditions. More specifically, the hydration catalyst 203 is of a type and is selected so as to cause the n-butenes (unreacted butenes in the mixture) to be hydrated into 2-Butanol and any remaining isobutene that is contained in the unreacted butene feed is hydrated into tert-Butanol. In other words, the hydration catalyst 203 is selected so as to be of a type that hydrates the butenes in the feedstock in the presence of water which is part of the mixture introduced into the hydration reactor 200. A mixed butanols product stream is produced as a result of the contact between the water and mixed butene mixture and the hydration catalyst.

The mixed butanols product stream then exits the hydration reactor 200 via conduit 205, through which the mixed butanols product stream travels to a high pressure separator 210. In the high pressure separator 210, the organic phase and the aqueous phase of the mixed butanols product stream are separated. The aqueous phase exits the high pressure separator 210 via conduit 211 and the organic phase exits via conduit 213. The aqueous phase represents a constituent of the stream that is not desired in the final olefin based product stream.

The aqueous phase, through conduit 211, travels to an azeotropic distillation column 220. In the azeotropic distillation column 220, the butanol-water azeotrope is distilled out of the aqueous mixture and recycled back into the high-pressure separator 210 via conduit 215. As is known, an azeotrope is a mixture of two or more liquids in such a way that its components cannot be altered by simple distillation. This happens because, when the azeotrope is boiled, the vapor has the same proportions of constituents as the unboiled mixture. There are a number of different techniques that can be used to separate the constituents of the azeotrope. One technique is azeotropic distillation in which an additional agent, called an entrainer, that will affect the volatility of one of the azeotrope constituents more than another. The azeotropic distillation column 220 uses this type of technique to separate the constituents (butanol and water). In the present arrangement, the remaining water in the azeotropic distillation column 220 exits via conduit 217 where it is then recycled back to the hydration reactor 200.

The organic phase of the mixed butanols product stream—made up of unreacted mixed butenes and mixed butanols—exits the high pressure separator 210 via conduit 213 and travels to a debutenizer 240. As is known, the debutenizer 240 is a type of fractional distillation column used to separate butenes from other components during the refining process. Distillation is the process of heating a liquid to vapor and condensing the vapors back to liquid in order to separate or purify the liquid. Fractional distillation, as occurs in a debutenizer, is the separation of a fraction—a set of compounds that have a boiling point within a given range—from the rest of the mixture.

In the debutenizer 240, the unreacted mixed butenes are separated from the mixed butanols. The unreacted mixed butenes exit the debutenizer via conduit 218 and are recycled back into the oligomerization reactor 110. The mixed butanols exit the debutenizer 240 via conduit 219, through which they travel to connect with the DIB product discharged through conduit 141 to form the final product identified at 300. It will be appreciated that this final product 300 which can be considered to be a product stream of RON enhanced mixed butanols can then undergo additional processing and/or transportation to another site, such as a storage site.

As a result of the two-stage (two-step) process design and the operating conditions in each of the reactors, along with the catalyst compositions in the reactors, the DIBs content in the mixed butanols product 300 can be altered (customized) in order to meet the blending requirements of the fuel. This ability to alter the DIBs content is not possible a simultaneous oligomerization/hydration process, such as that described in applicant's own previous U.S. patent application publication No. 2013/0104449 (the '449 publication). In such simultaneous process, the mixed butenes feed stream is combined with water before being introduced into a common reactor which operates under oligomerization and hydration conditions to convert the mixed olefins into alcohols (e.g., butenes into butanols) and simultaneously dimerize the mixed olefins into oligomers, such as DIBs. Since two different processes, namely oligomerization and hydration, occur in the same reactor, the mixed olefins, and in particular, isobutene, are both oligomerized and hydrated resulting in a mixed butanols and DIB product stream. Since DIB production is also in the context of a competing and simultaneous hydration process, the content of DIBs is not optimized and cannot be independently controlled to yield a desired product stream with optimal amount of DIBs. In contrast, the present invention achieves these objectives.

More specifically and according to one embodiment, as a result of oligomerization catalyst and reaction conditions, at least a majority of and preferably, at least a substantial portion of the isobutene present in the mixed butene feed is oligomerized in the first reactor. The conversion percentage of isobutene is between 30-100%. The mixed butanols product formed in the second stage is later combined with the DIB from the first stage to create the final product, which can be used as a superior gasoline constituent.

Thus, one will appreciate that one advantage of the present invention is the ability to produce DIBs and mixed butanols in a common scheme that implements a single two-step process with each stage (step) being independent from the other. Alcohols (e.g., butanols) and DIBs can both be prepared from the isobutene in the initial mixed butenes feed stream, but there have not been any butene hydration processes in place that efficiently convert mixed butenes into butanols while, at the same time, dimerizing part of the butene feed into oligomers, such as DIBs. As mentioned above, the '449 publication addresses this same issue by simultaneously hydrating and oligomerizing mixed butenes to produce alcohols and DIBs. However, the advantage of the present invention over the '449 publication is that the present invention provides better control over the composition of DIBs in the final product since the first stage maximizes DIBs formation and the DIBs is later combined with the alcohols (butanols) from stage two. Specifically, by increasing the DIB content of the final product, the concentration of tert-butanol, which has poorer blending properties compared with 2-butanol and DIBs, is reduced.

Another advantage is that the products of the present invention can be used as superior gasoline constituents without separation. The mixed butanols serve as oxygenated octane enhancers to provide for increased combustion efficiency, thereby reducing emissions. The DIBs complement the mixed butanols by serving as high energy content octane enhancers and low RVP gasoline components.

Figure 2:
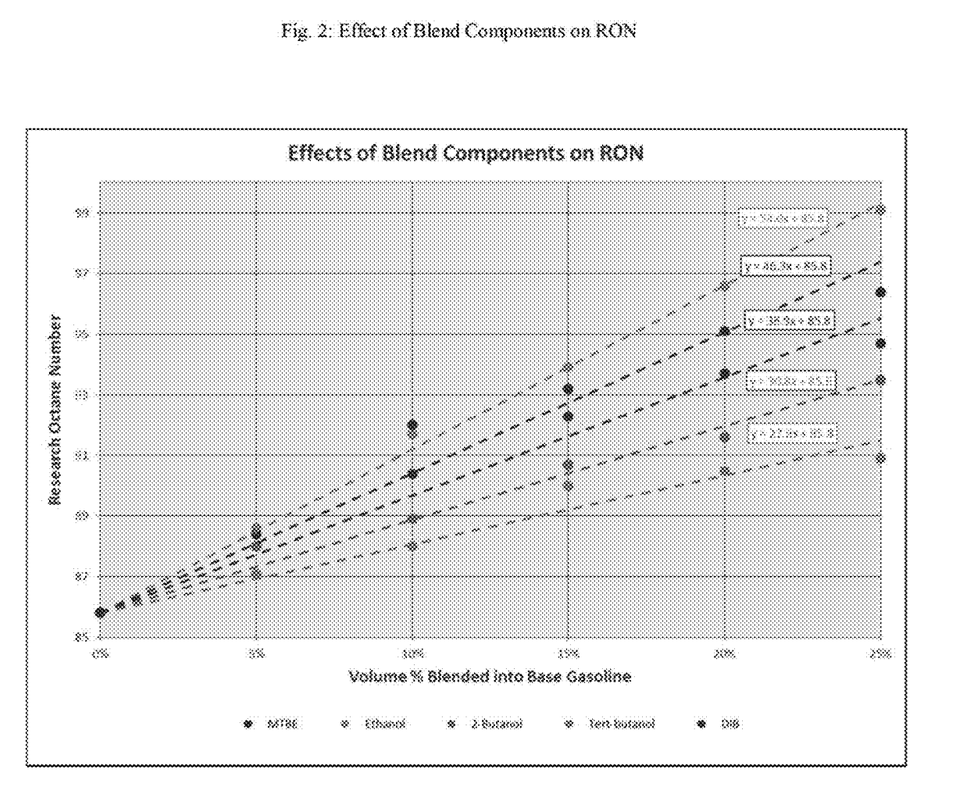
FIG. 2 is a graph showing the effect of various exemplary blend components on RON.

The advantageous qualities of DIBs and butanols as gasoline components compared with other known gasoline components are further explained by the data in Table 1 and FIG. 2. This data stems from an experiment in which the five compounds listed below (MTBE, ethanol, 2-butanol, tert-butanol, and DIB) are each blended into a base gasoline in concentrations of 5, 10, 15, 20, and 25%, respectively, and their respective characteristics are determined. In particular, Table 1 sets forth the trends in RON, Mon, octane sensitivity, and RVP, respectively.

TABLE 1

Blending Properties Comparison for Common Fuel Blends

| Blends | Blending RON | Blending MON | Blending Sensitivity | Energy Density or Higher Heating Value (MJ/Kg) | RVP 15% v/v Blend |
|---|---|---|---|---|---|
| Base gasoline | 85.8 | 81.0 | 4.8 | 45.6 | 9.46 |
| MTBE | 124.7 | 103.5 | 21.2 | 38.0 | 9.6 |
| Ethanol | 139.8 | 106.6 | 33.2 | 29.9 | 11.5 |
| 2-Butanol | 116.6 | 97.8 | 18.8 | 37.3 | 10.4 |
| tert-butanol | 108.6 | 89.3 | 19.3 | 37.3 | 9.96 |
| DIB | 132.1 | 99.2 | 32.9 | 48.2 | 8.5 |

As shown by Table 1 and FIG. 2, compared with other common fuel constituents, DIB has the lowest RVP, the highest energy density, the second highest blending RON, and the second highest blending octane sensitivity (essentially equivalent to that of ethanol). Additionally, 2-butanol and tert-butanol have blending octane sensitivities and energy densities comparable to MTBE, and result in a lower RVP at 15% concentrations than ethanol. Based on this data, it can be inferred that increasing the DIB content of the mixed butanols product stream improves its blend properties by enhancing RON, octane sensitivity, and energy density while decreasing the RVP. Thus, the combination of DIBs and butanols creates a high-octane fuel additive with the potential to replace ethanol as a superior oxygenate and the present invention allows for optimization of DIBs content due to the two-step process scheme described herein.

As mentioned, the alcohols and oligomers in the product stream made in accordance with the embodiment of the present invention can be used as a component in fuel compositions or as a neat fuel composition. For example, in one embodiment, a neat fuel composition can be prepared according to the methods described herein that include a mixed butanol fuel having an octane rating suitable for use in combustion or compression engines. In another embodiment, a fuel composition that includes a fuel component and a mixed butanol fuel is provided. In an embodiment, the fuel component can include gasoline, diesel, jet fuel, aviation gasoline, heating oil, bunker oil, or combination thereof. In an aspect, the mixed butanols can include n-butanol, 2-(+/−)-butanol, iso-butanol, tert-butanol, or combination thereof; or alternatively, 2-(+/−)-butanol and tert-butanol. In certain embodiments, the mixed butanols can include at least two butanol compounds selected from n-butanol, 2-(+/−)-butanol, iso-butanol, tert-butanol, or combination thereof; or alternatively, 2-(+/−)-butanol and tert-butanol.

The mixed alcohols (butanols) stream made in accordance with the various embodiments of the present invention can be used in other types of fuel compositions, as will be apparent to those skilled in the art and are to be considered within the scope of the present invention.

As described herein, the process and system of the present invention can be thought of as being, according to one embodiment, a selective oligomerization of isobutene in the presence of the other butene isomers and in the absence of water and the hydration of all four butene isomers together in the presence of water (i.e., 1-butene, trans-2-butene, isobutene and cis-2-butene) with the oligomerization and hydration reactions implemented in two separate reactors.

The process and the system of the present invention provide a number of advantages over the conventional oligomerization and hydration processes. These advantages include but are not limited to: (1) providing an alternative gasoline oxygenate that possesses comparable RON enhancement properties and higher energy content than MTBE and ethanol, while eliminating the associated compatibility and contamination issues; (2) utilizing the products of the present invention—namely, DIBs and mixed butanols—as superior gasoline constituents without separation; and (3) providing better control over the composition of DIBs in the mixed butanols final product than previous methods for simultaneously oligomerizing and hydrating mixed olefin feeds.

EXAMPLES

The following examples are provided to better illustrate embodiments of the present invention, but they should not be construed as limiting the scope of the present invention.

The following experiments were conducted at a pilot plant having the configuration and characteristics of the system shown in FIG. 1. The reaction conditions for Examples 1 and 2 are listed in the below Table 2.

Example 1

The catalyst used for both the oligomerization stage and the hydration stage was an ion-exchange resin and more particularly, the catalyst was an ion-exchange resin that is commercially available under the trade name 0008-3 from Kairui Chemicals Co. Ltd of China. This exemplary resin is a macroporous strong acid cation exchange resin which is made up of opaque beads and is a sulfonic acid cation exchanger in hydrogen form. A total of 30 mL of catalyst was loaded. The mixed butenes were purchased from a local gas company and used without any purification. The composition of the butene mixture (the mixed butenes) is 1-butene 21%, isobutene 35%, 2-cis-butene 19% and 2-trans-butene 25%. The unreacted butenes were analyzed by an online gas chromatography which could be fed into the second stage of hydration reactor.

Example 2

The catalyst used for both the oligomerization stage and the hydration stage was a heteropoly acid catalyst and more particularly, the catalyst was a Cs salt of a heteropoly acid which is synthesized according to the process described in U.S. Ser. No. 14/092,601 and described in Miao Sun, Jizhe Zhang, Chuanjing Cao, Qinghong Zhang, Ye Wang, Huilin Wan. Applied Catalysis A: General 349 (2008) 212-221).

TABLE 2

| Example 1: Catalyst Kairui 008-3 | | | | | | | | |
|---|---|---|---|---|---|---|---|---|
| Reaction Conditions: Temperature: 40° C.; pressure: 20 bar; LHSV: 0.63 hr-1; test period: 780 min | | | | | | | | |
| Total butenes | Products selectivity (%) | | | | Tail gas composition for the hydration reactor | | | |
| conversion % | C8 olefins | C12 olefins | C16 olefins | C20 olefins | 2-trans-butene | 1-butene | iso-butene | 2-cis-butene |
| 42.8 | 88.2 | 9.3 | 2.6 | 0 | 37.78 | 31.5 | 2.77 | 27.95 |
| Example 2: catalyst Cs-HPA | | | | | | | | |
| Reaction Conditions: Temperature: 40° C.; pressure: 20 bar; LHSV: 0.63 hr-1; test period: 405 min | | | | | | | | |
| Total butenes | Products selectivity (%) | | | | Tail gas composition for the hydration reactor | | | |
| conversion (%) | C8 olefins | C12 olefins | C16 olefins | C20 olefins | 2-trans-butene | 1-butene | iso-butene | 2-cis-butene |
| 43.7 | 65.1 | 29.8 | 4.5 | 0.5 | 38.26 | 30.2 | 3.08 | 28.46 |

The results of Examples 1 and 2 demonstrate that isobutene can be selectively converted into DIBs. The butenes composition after the oligomerization reactor is significantly changed. The iso-butene content is reduced over 90% in the feed stream.

Example 3

The catalyst for Example 3 is the same catalyst used in Example 1. Example 3 demonstrates that at a higher dimerization temperature, all of the isomers of butenes can be oligomerized. However, isobutene is more prone to be converted into oligomers. Results and conditions are shown in the below Table 3.

TABLE 3

Example 3: Catalyst Kairui 008-3

Reaction Conditions: 160° C.; pressure: 20 bar; LHSV: 0.33 hr-1;
test period: 1020 min

| Total butenes conversion % | Products selectivity (%) | | | | Tail gas composition for the hydration reactor | | | |
|---|---|---|---|---|---|---|---|---|
| | C8 olefins | C12 olefins | C16 olefins | C20 olefins | 2-trans-butene | 1-butene | iso-butene | 2-cis-butene |
| 78 | 58.5 | 31.9 | 8.2 | 1.4 | 59.36 | 10 | 0.91 | 29.73 |

While the present invention has been described above using specific embodiments, there are many variations and modifications that will be apparent to those having ordinary skill in the art. As such, the described embodiments are to be considered in all respects as illustrative, and not restrictive. Therefore, the scope of the invention is indicated by the appended claims, rather than by the foregoing description. All changes that come within the meaning and range of equivalency of the claims are to be embraced within their scope.

What is claimed is:

1. A two-stage process for oligomerizing and hydrating a hydrocarbon feed comprising mixed olefins including mixed butenes including isobutene and n-butenes, the process comprising the steps of:
    introducing the hydrocarbon feed into a first reactor vessel under reaction conditions that are operable to oligomerize the isobutene into diisobutenes;
    contacting the mixed hydrocarbon feed with an oligomerization catalyst within the first reactor vessel, the oligomerization catalyst being of a type that selectively oligomerizes the isobutene into diisobutenes;
    separating the diisobutenes from unreacted butenes to form a diisobutene stream;
    introducing the unreacted butenes into a second reactor vessel in the presence of water and under reaction conditions that operable to hydrate the unreacted butenes including the unreacted n-butenes and any unreacted isobutene;
    contacting the unreacted butenes with a hydration catalyst within the second reactor vessel to hydrate the unreacted butenes to form a mixed butanols stream; and
    combining the diisobutene stream and mixed butanols stream to form a product stream.

2. The two-stage process of claim 1, wherein the n-butenes comprise 1-butene, 2-trans-butene, and 2-cis-butene.

3. The two-stage process of claim 1, wherein the hydrocarbon feed is introduced into the first reactor vessel in the absence of water.

4. The two-stage process of claim 1, wherein prior to introducing the hydrocarbon feed into the first reactor vessel, the hydrocarbon feed passes through: (a) a first compressor which compresses the hydrocarbon feed to a first predetermined pressure; and (b) a first heat exchanger that adjusts a temperature of the hydrocarbon feed to a first predetermined temperature.

5. The two-stage process of claim 4, wherein the first predetermined pressure is between about 5 bar and 100 bar and the first predetermined temperature is between about 30° C. and about 250° C.

6. A two-stage process for oligomerizing and hydrating a hydrocarbon feed comprising mixed olefins including mixed butenes including isobutene and n-butenes, the process comprising the steps of:
    introducing the hydrocarbon feed into a first reactor vessel under reaction conditions that are operable to oligomerize the butenes;
    contacting the mixed hydrocarbon feed with an oligomerization catalyst within the first reactor vessel, the oligomerization catalyst being of a type that selectively oligomerizes isobutene into diisobutenes;
    separating the diisobutenes from unreacted butenes to form a diisobutene stream, wherein the step of separating the diisobutenes from the unreacted butenes comprises the step of:
        introducing the diisobutenes and the unreacted butenes from the first reactor vessel into a low pressure separator that is configured to separate the diisobutenes from the unreacted butenes including unreacted n-butenes and any unreacted isobutene;
    introducing the unreacted butenes into a second reactor vessel in the presence of water and under reaction conditions that operable to hydrate the unreacted butenes including the unreacted n-butenes and any unreacted isobutene;
    contacting the unreacted butenes with a hydration catalyst within the second reactor vessel to hydrate the unreacted butenes to form a mixed butanols stream; and
    combining the diisobutene stream and mixed butanols stream to form a product stream.

7. The two-stage process of claim 6, wherein prior to introducing the unreacted butenes into the second reactor vessel, water is added to the unreacted butenes, including the unreacted n-butenes, to form a first an aqueous mixture that passes through: (a) a compressor which compresses the first aqueous mixture to a predetermined pressure; and (b) a heat exchanger that adjusts a temperature of the aqueous mixture to a predetermined temperature.

8. The two-stage process of claim 7, wherein the predetermined pressure is between about 10 bar and 100 bar and the predetermined temperature is between about 80° C. and about 250° C.

9. The two-stage process of claim 1, wherein the step of contacting the unreacted butenes with a hydration catalyst within the second reactor vessel results in the n-butenes being hydrated to 2-butanol and any isobutene being hydrated to tert-butanol.

10. The two-stage process of claim 1, further including the steps of: (a) passing the mixed butanols stream from the second reaction vessel through a high pressure separator which is configured to separate an organic phase containing unreacted mixed butenes along with extracted mixed butanols from an aqueous phase that is saturated with mixed butanols; (b) passing the separated organic phase through a debutenizer column in which the organic phase is separated and unreacted mixed butenes are removed; and (c) passing the separated aqueous phase to an azeotropic distillation column in which alcohol-water azeotrope is distilled out of the aqueous phase.

11. The two-stage process of claim 10, wherein the unreacted mixed butenes removed from the debutenizer are recycled and combined with the hydrocarbon feed upstream of the first reactor vessel and the alcohol-water azeotrope is recycled back to the high pressure separator for further recover alcohols while water is recycled back to a location upstream of the second reactor vessel.

12. The two-stage process of claim 1, wherein the oligomerization conditions can be varied independent from the hydration conditions to maximize diisobutene formation in the first reactor vessel from 5 mol % to a maximum of up to 100 mol % of isobutene in the hydrocarbon feed.

13. The two-stage process of claim 1, wherein a conversion rate of converting isobutene to diisobutene in the first reactor vessel is between about 5 mol % and about 100 mol %.

14. The two-stage process of claim 1, wherein the hydrocarbon feed consists essentially of butenes.

15. The two-stage process of claim 1, further comprising the step of combining the product stream with a gasoline stream to produce a gasoline product having increased research octane number (RON) and reduced Reid vapor pressure (RVP) as compared to a second gasoline product having an absence of the product stream.

16. The two-stage process of claim 1, wherein each of the oligomerization catalyst and the hydration catalyst comprises at least one of an acidic catalyst and substituted/non-substituted heteropoly acids.

17. The two-stage process of claim 16, wherein the acidic catalyst comprises an ionic exchange resin.

18. The two-stage process of claim 1, wherein the oligomerization catalyst and hydration catalyst are the same.

19. The two-stage process of claim 1, wherein the conversion rate of converting isobutene to diisobutene in the first reactor vessel is greater than 90%.

20. A two-stage process for oligomerizing and hydrating a hydrocarbon feed comprising mixed olefins including mixed butenes including isobutene and n-butenes, the process comprising the steps of:
introducing the hydrocarbon feed into a first reactor vessel under reaction conditions that are operable to oligomerize the butenes;
contacting the mixed hydrocarbon feed with an oligomerization catalyst within the first reactor vessel, the oligomerization catalyst being of a type that selectively oligomerizes butenes into oligomers;
separating the oligomers from unreacted butenes, to form an oligomer stream;
introducing the unreacted butenes into a second reactor vessel in the presence of water and under reaction conditions that operable to hydrate the unreacted butenes including the unreacted n-butenes and any unreacted isobutene;
contacting the unreacted butenes with a hydration catalyst within the second reactor vessel to hydrate the unreacted butenes to form a mixed butanols stream;
passing the mixed butanols stream from the second reaction vessel through a high pressure separator which is configured to separate an organic phase containing unreacted mixed butenes along with extracted mixed butanols from an aqueous phase that is saturated with mixed butanols;
passing the separated organic phase through a debutenizer column in which the organic phase is separated and unreacted mixed butenes are removed;
passing the separated aqueous phase to an azeotropic distillation column in which alcohol-water azeotrope is distilled out of the aqueous phase; and
combining the oligomer stream and mixed butanols from the debutenizer to form a product stream.

21. The two-stage process of claim 1, wherein the isobutene comprises 35% of the composition of the mixed butenes.

22. The two-stage process of claim 21, wherein the unreacted mixed butenes removed from the debutenizer are recycled and combined with the hydrocarbon feed upstream of the first reactor vessel and the alcohol-water azeotrope is recycled back to the high pressure separator for further recover alcohols while water is recycled back to a location upstream of the second reactor vessel.

23. The two-stage process of claim 4, wherein prior to introducing the unreacted butenes into the second reactor vessel, water is added to the unreacted butenes, including the unreacted n-butenes, to form an aqueous mixture that passes through: (a) a second compressor which compresses the aqueous mixture to a second predetermined pressure; and (b) a second heat exchanger that adjusts a temperature of the aqueous mixture to a second predetermined temperature.

* * * * *